(12) United States Patent
Melsheimer et al.

(10) Patent No.: US 8,568,433 B2
(45) Date of Patent: Oct. 29, 2013

(54) MEDICAL DEVICE HAVING ONE OR MORE ACTIVE STRANDS

(75) Inventors: Jeffry S. Melsheimer, Springville, IN (US); Bradley K. Butler, Spencer, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 283 days.

(21) Appl. No.: 12/500,836

(22) Filed: Jul. 10, 2009

(65) Prior Publication Data

US 2011/0009806 A1 Jan. 13, 2011

(51) Int. Cl.
*A61B 17/32* (2006.01)
*A61B 17/28* (2006.01)

(52) U.S. Cl.
USPC ............................... 606/170; 606/1; 606/205

(58) Field of Classification Search
USPC ......... 606/108, 113, 114, 127, 128, 139, 142, 606/143, 144, 159, 167–180, 184, 185, 606/191–200, 205–209, 1; 600/201–209
See application file for complete search history.

(56) References Cited

U.S. PATENT DOCUMENTS

| | | | | |
|---|---|---|---|---|
| 3,799,152 A | * | 3/1974 | Kim | ................ 600/139 |
| 4,198,960 A | * | 4/1980 | Utsugi | ............ 600/104 |
| 4,569,347 A | | 2/1986 | Frisbie | |
| 4,637,396 A | | 1/1987 | Cook | |
| 4,921,484 A | | 5/1990 | Hillstead | |
| 4,936,826 A | | 6/1990 | Amarasinghe | |
| 5,078,723 A | * | 1/1992 | Dance et al. | ............ 606/159 |
| 5,104,388 A | | 4/1992 | Quackenbush | |
| 5,211,654 A | | 5/1993 | Kaltenbach | |
| 5,257,974 A | | 11/1993 | Cox | |
| 5,695,469 A | | 12/1997 | Segal | |
| 5,718,159 A | * | 2/1998 | Thompson | ........... 87/33 |
| 5,849,037 A | * | 12/1998 | Frid | ................ 623/1.2 |
| 5,984,929 A | * | 11/1999 | Bashiri et al. | .......... 606/108 |
| 6,080,141 A | | 6/2000 | Castro et al. | |
| 6,083,257 A | * | 7/2000 | Taylor et al. | .......... 623/1.46 |
| 6,197,013 B1 | * | 3/2001 | Reed et al. | ............. 604/509 |
| 6,355,013 B1 | | 3/2002 | Van Muiden | |
| 6,416,529 B1 | | 7/2002 | Holman et al. | |
| 6,939,327 B2 | | 9/2005 | Hall et al. | |

(Continued)

FOREIGN PATENT DOCUMENTS

EP 1 772 167 4/2007
JP 2002 275774 9/2002

OTHER PUBLICATIONS

International Search Report and Written Opinion for PCT/US2010/040746 mailed Dec. 27, 2010; 16 pgs.

(Continued)

*Primary Examiner* — Kathleen Holwerda
(74) *Attorney, Agent, or Firm* — Brinks Hofer Gilson & Lione

(57) ABSTRACT

The present embodiments provide an elongate medical device comprising a plurality of strands twisted in a generally helical manner to form a tubular shape having a longitudinal axis. A first strand of the plurality of strands is moveable with respect to at least a second strand of the plurality of strands. Actuation of the one or more strands may perform a medical function or actuate an associated distal component. A working lumen of the tubular member may remain unobstructed for delivery of medical components or fluids.

12 Claims, 11 Drawing Sheets

(56) References Cited

U.S. PATENT DOCUMENTS

| | | | |
|---|---|---|---|
| 8,298,257 B2 * | 10/2012 | Sepetka et al. | 606/200 |
| 2001/0044633 A1 | 11/2001 | Klint | |
| 2002/0072791 A1 * | 6/2002 | Eder et al. | 623/1.15 |
| 2006/0178685 A1 | 8/2006 | Melsheimer | |
| 2006/0195137 A1 * | 8/2006 | Sepetka et al. | 606/200 |
| 2008/0262532 A1 * | 10/2008 | Martin | 606/200 |

OTHER PUBLICATIONS

International Preliminary Report on Patentability for PCT/US2010/040746 mailed Jan. 19, 2012; 10 pgs.

* cited by examiner

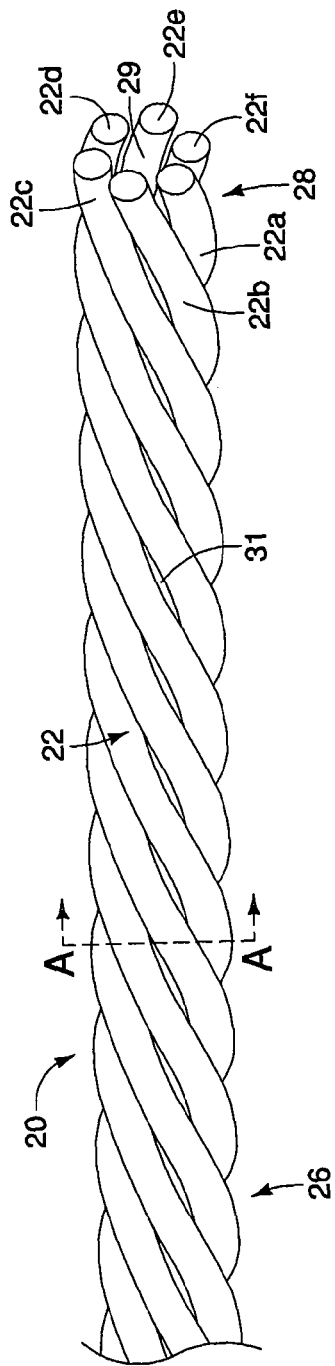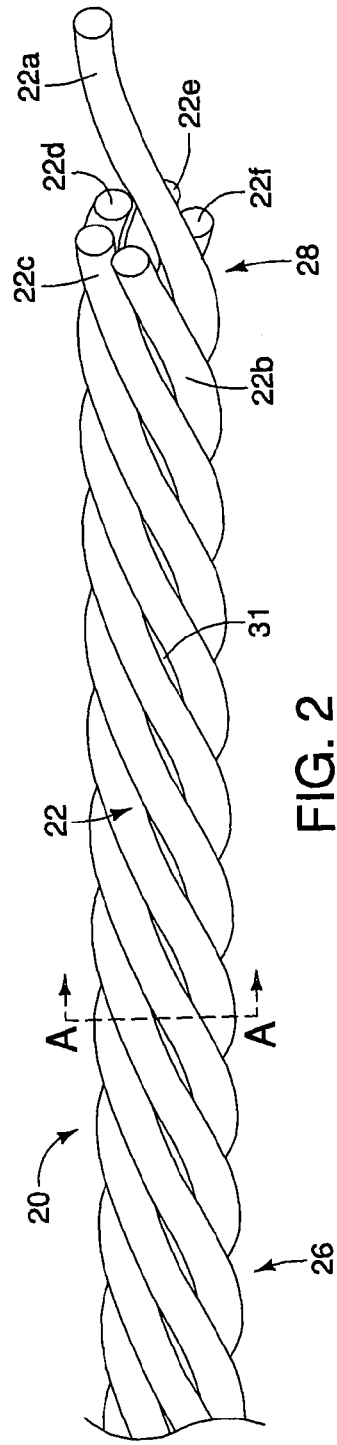
FIG. 1
FIG. 2

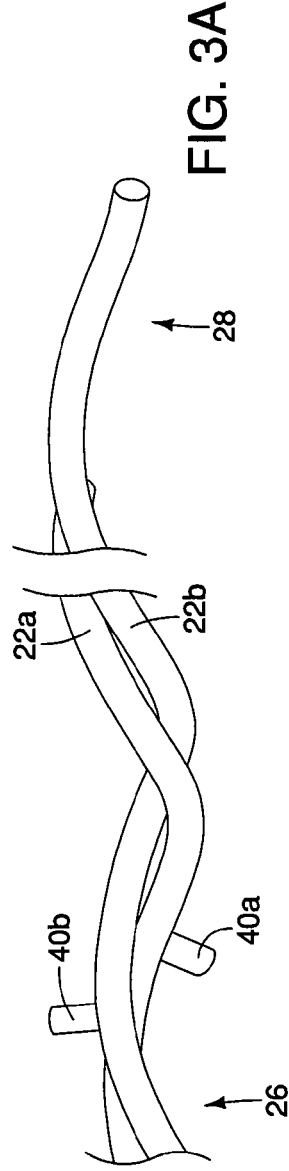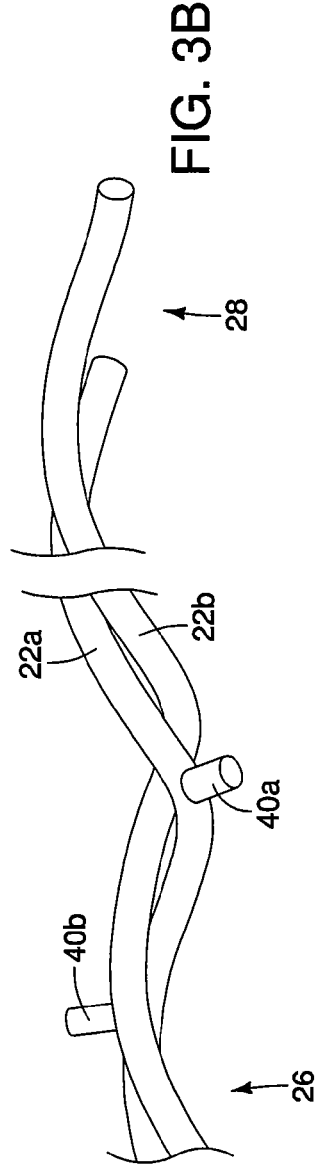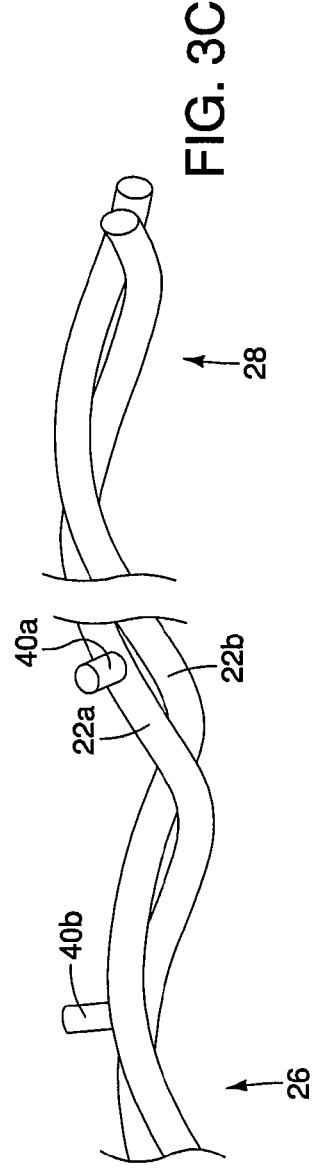

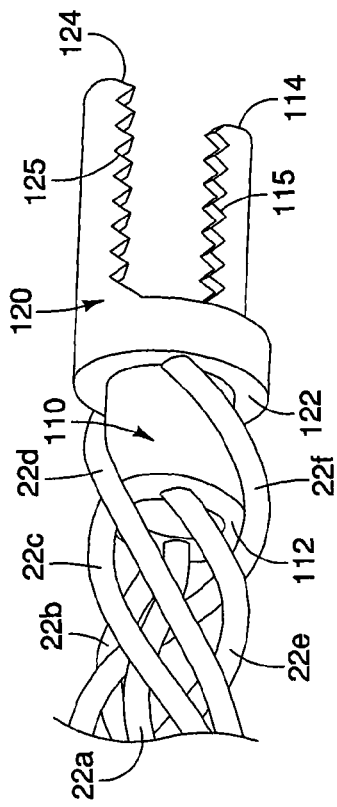
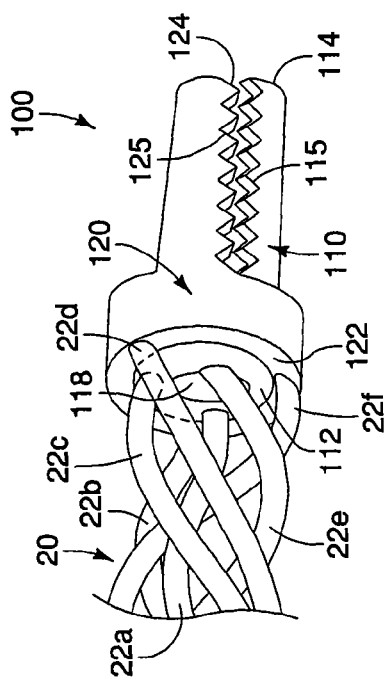

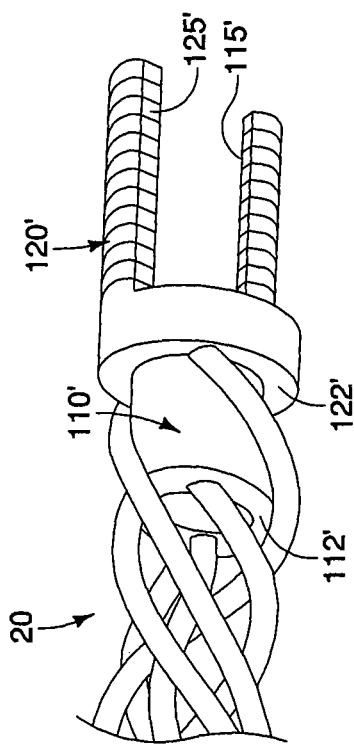
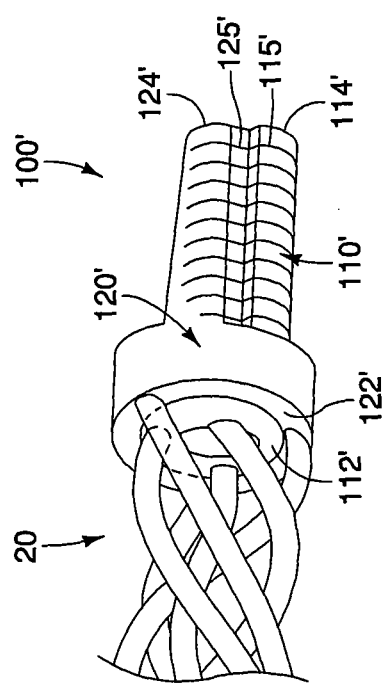

MEDICAL DEVICE HAVING ONE OR MORE ACTIVE STRANDS

BACKGROUND

The present embodiments relate generally to the field of medical devices, and more particularly, to a multi-stranded tubular device for use during a medical procedure.

Various medical conditions may affect patients in an array of bodily passageways, such as vessels and ducts. In several instances, it may be desirable to insert a tubular medical device, such as a catheter or overtube, into the passageway as part of a medical procedure. The tubular device may comprise a generally cylindrical shape having an outer surface and one or more lumens.

Generally, various medical components may be delivered to a target site through one or more of the lumens of the tubular device. Solely by way of example, a snare, cutting device, visualization device, or numerous other components may be advanced through the lumen of the tubular device towards the target site. The medical components then may be advanced, retracted and/or rotated during the process of treating or visualizing the medical condition. If a co-axial system is used to deploy a medical component, then multiple tubes are delivered within a single lumen of the tubular device and actuated with respect to each other to achieve a desired effect.

When such medical components are delivered and used, they typically obstruct substantially the entirety of a particular lumen of the tubular device. For example, if a snare or cutting device is delivered through a given lumen, the outside diameter of the snare or cutting device, or an associated actuating member such as a wire or cable, may be only slightly smaller than the diameter of the lumen. Accordingly, there may be little additional space within a particular lumen, and thus only one component may be delivered and actuated at any given time. Notably, if a co-axial deployment system is delivered within a given lumen, it also would obstruct substantially the entirety of that lumen.

Increasing the overall diameter of the tubular device, to thereby increase the diameter of a working lumen, is not always a viable option because it may prohibit introduction of the tubular device in smaller vessels. Thus, many medical systems are limited in the amount of available working lumen space when medical components and associated actuation members are implemented during a procedure.

SUMMARY

The present invention provides an elongate medical device comprising a plurality of strands twisted in a generally helical manner to form a tubular shape having a longitudinal axis. A first strand of the plurality of strands is moveable with respect to at least a second strand of the plurality of strands. A central working lumen may be formed within the plurality of strands and along the longitudinal axis, and may be sized for the delivery of at least one medical component.

In one embodiment, a first group of strands comprises at least two of the plurality of strands. The first group of strands is coupled together so that individual strands move in unison with each other. Similarly, a second group of strands comprising at least another two of the plurality of strands is coupled together so that those particular strands move in unison with each other. In use, the first group of strands is movable with respect to the second group of strands.

A first coupling assembly may operatively couple each strand of the first group of strands together, and a second coupling assembly may operatively couple each strand of the second group of strands together. The first and second coupling assemblies may be independently engaged to selectively actuate the first and second group of strands, respectively.

Various medical components may be coupled to the distal regions of the plurality of strands to perform a desired function. For example, in one embodiment, a cutting device having first and second segments is used, where the first segment is coupled to the first group of strands and the second segment is coupled to the second group of strands. In use, independent actuation of the first and second groups of strands, relative to each other, yields a corresponding movement of the first and second segments of the cutting device.

In an alternative embodiment, a first strand of the plurality of strands may comprise an integral fiber optic component. Actuation of the first strand, relative to the other strands, may permit longitudinal and rotational movement of the first strand, thereby enabling imaging in longitudinal and rotational directions.

Advantageously, the present embodiments provide a tubular device having one or more active strands that are capable of performing a function for an associated medical component. Since actuation of the one or more active strands does not affect the central working lumen of the tubular device, the working lumen remains unobstructed during use of the one or more components.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following figures and description. The components in the figures are not necessarily drawn to scale, emphasis instead being placed upon illustrating the principles of the invention. Moreover, in the figures, like referenced numerals designate corresponding parts throughout the different views.

FIG. 1 is a perspective view of a first embodiment of an elongate medical device having a plurality of strands.

FIG. 2 is a perspective view of the medical device of FIG. 1 wherein one strand is advanced with respect to the other strands.

FIGS. 3A-3C are side perspective views showing a first strand being sequentially advanced with the respect to a second strand.

FIGS. 9A-9B are perspective views of an assembly that may be coupled to the medical device of FIG. 1, as shown in retracted and advanced states, respectively.

FIGS. 10A-10B are perspective views of an alternative assembly that may be coupled to the medical device of FIG. 1, as shown in retracted and advanced states, respectively.

DETAILED DESCRIPTION OF THE PREFERRED EMBODIMENTS

In the present application, the term "proximal" refers to a direction that is generally towards a physician during a medical procedure, while the term "distal" refers to a direction that is generally towards a target site within a patient's anatomy during a medical procedure.

Referring now to FIGS. 1-2, a first embodiment of an elongate medical device 20 is shown. The elongate medical device 20 generally comprises a plurality of elongate strands 22. In the embodiments shown herein, six exemplary strands 22a-22f are shown. However, as will be explained in further detail below, any suitable number of strands 22 may be employed.

Figure 4A:
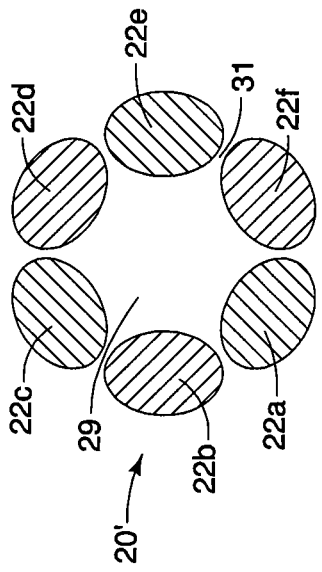
FIGS. 4A-4D are cross-sectional views along line A-A of FIGS. 1-2, each depicting alternative cross-sectional shapes of the strands 22a-22f.

In the embodiment of FIGS. 1-2, the strands 22a-22f are twisted in a generally helical manner to form a tubular shape. A working lumen 29 is formed in a central region between the strands 22a-22f, as best seen in FIG. 4A below. As will be explained in further detail below, various medical components may be advanced through the working lumen 29 to a target site.

Gaps 31 optionally may be formed between the individual strands 22a-22f when they are twisted about one another, as depicted in FIGS. 1-2. The gaps 31 may be sized to provide at least some flexibility to allow the strands 22a-22f to move with respect to one another, or alternatively, the gaps 31 may be substantially eliminated along one or more regions of the device 20 to provide one or more corresponding taut regions. In effect, the interweaving of the strands 22a-22f with respect to one another may be manipulated to vary strength or flexibility characteristics along the device. Further, a sheath or liner may be disposed over a portion of the strands 22a-22f to help keep the strands together or vary the stiffness along the device, preferably without substantially interfering with the movement of the strands 22a-22f. The strands 22a-22f may be undersized relative to the sheath or liner to facilitate movement therein. Further, outer surfaces of each of the strands 22a-22f may be coated for lubricity to facilitate movement with respect to one another. A lubricious material such as Teflon® may be heat-shrunk over the individual strands 22a-22f to facilitate movement of the strands.

Each of the strands 22a-22f comprises a proximal region 26 and a distal region 28. When the proximal region 26 of a particular strand is actuated, the distal region 28 of the corresponding strand may be maneuvered in both longitudinal and rotational directions. For example, referring to FIG. 2, an individual strand 22f has been advanced distally and rotationally with respect to the remaining five strands by actuating the proximal region 26 of the strand 22f and holding the remaining five strands stationary. Notably, the distal region 28 of the strand 22f is not only advanced distally, but also in an angular direction with respect to its previous position in FIG. 1.

Referring now to FIGS. 3A-3C, the relationship between only two strands 22a and 22b are shown for purposes of illustration. As can be seen, the two strands 22a and 22b are twisted in a generally helical manner with respect to each other. In FIG. 3A, the distal end of the first strand 22a is proximal to the distal end of the second strand 22b. In FIGS. 3B-3C, the first strand 22a is sequentially advanced with the respect to the second strand 22b. As can be seen, the distal region 28 of the strand 22a is not only advanced distally in FIG. 3C, but also in an angular direction with respect to its original position in FIG. 3A. It should be noted that while FIGS. 3A-3C depict the advancement of a strand 22a relative to a stationary strand 22b, the strand 22b could have been retracted or advanced while the strand 22a is held stationary, or alternatively both strands 22a and 22b may have been actively advanced with respect to each other, in the same or different directions. The same general principles apply to the six-strand embodiments of FIGS. 1-2 above and FIGS. 4-9 below.

Referring to FIG. 4A, in one embodiment, each of the strands 22a-22f comprises a generally circular cross-sectional shape having an identical diameter. Regardless of the advancement of one or more strands 22a-22f with respect to each other, the working lumen 29 remains an unobstructed passageway. In lieu of the cross-sectional shape shown in FIG. 4A, the strands 22a-22f may comprise cross-sectional shapes that are square, triangular, pie-shaped, truncated cone, and the like. Further, while the strands 22a-22f are shown as having substantially identical cross-sectional sizes, some strands 22a-22f may comprise larger dimensions, such as cross-sectional diameters and/or tapers relative to other strands 22a-22f.

Figure 4B:
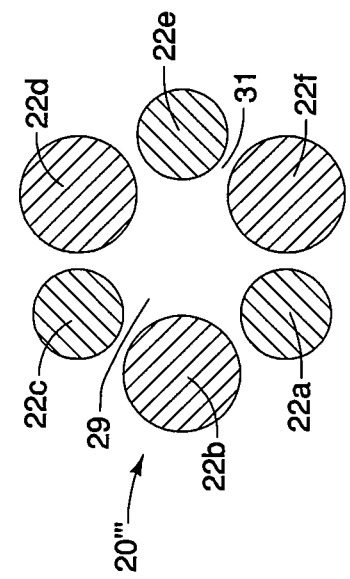
Figure 4C:
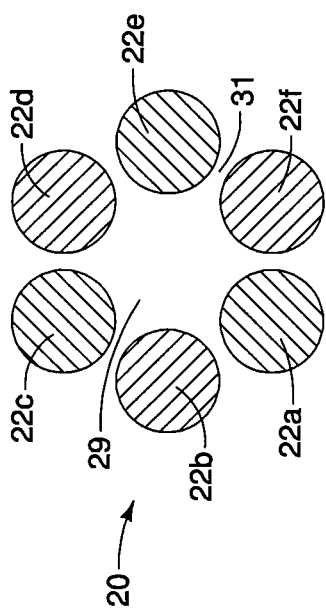

In another exemplary embodiment, shown in FIG. 4B, an alternative medical device 20' comprises strands having an elliptical cross-sectional shape, with the narrower portions of the ellipse adjacent to one another, which may increase the size of the lumen 29. A further alternative medical device 20" comprises strands having a tapered cross-sectional profile, as shown in FIG. 4C. In this latter embodiment, the strands may taper from a reduced profile at an inner region to a larger profile at an outer region, generally resembling a circular shape with linear gaps 31 separating adjacent strands 22a-22f. In FIG. 4C, the tapered cross-sectional shape of the adjacent strands may reduce or eliminate radially inward movement of one strand with respect to another and/or increase the cross-sectional area of the lumen.

Figure 4D:
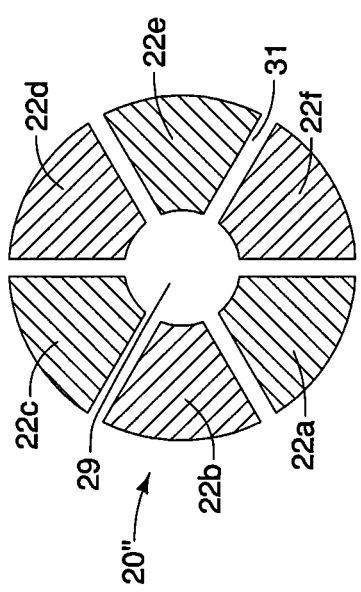

Referring to FIG. 4D, a further alternative medical device 20''' comprises strands 22a, 22c and 22e having smaller cross-sectional diameters relative to the plurality of strands 22b, 22d and 22f. The arrangement of FIG. 4D may be particularly useful where alternating strands 22 are active and fixed. For example, as explained in FIGS. 6-8 below, strands 22b, 22d and 22f may be active strands that are advanced in unison with respect to fixed strands 22a, 22c and 22e, or vice versa. Alternatively, both groups of strands may be movable in proximal and distal directions, either simultaneously or independently with respect to one another.

Moreover, the proximal region 26 and the distal region 28 of each strand 22a-22f may be formed from the same material, for example, comprising shape-memory characteristics. If a shape-memory material is employed, the medical device 20 may be heat-treated so that the distal region 28 of one or more strands 22a-22f assumes a predetermined deployed configuration when advanced relative to the other strands and/or no longer restrained by an optional sheath. Alternatively, the distal region 28 of one or more strands 22a-22f may be made from other metals and alloys that are biased to return to their relaxed, expanded configuration upon actuation. Solely by way of example, the distal region 28 of each strand 22a-22f may comprise other materials such as stainless steel, cobalt-chrome alloys, amorphous metals, tantalum, platinum, gold and titanium. The distal region 28 of each strand 22a-22f also may be made from non-metallic materials, such as thermoplastics and other polymers.

Referring now to FIGS. 5-8, one exemplary proximal assembly for actuating one or more of the strands 22a-22f is described. Unlike the embodiment of FIG. 2, in which a single strand 22f was advanced independently of the other five strands, various groups of strands are movably coupled together in the embodiment of FIGS. 5-8. For example, the strands 22a, 22c and 22e of a first strand group are moveably coupled to one another, while the alternating strands 22b, 22d and 22f of a second strand group are movably coupled to one another.

Figure 5:
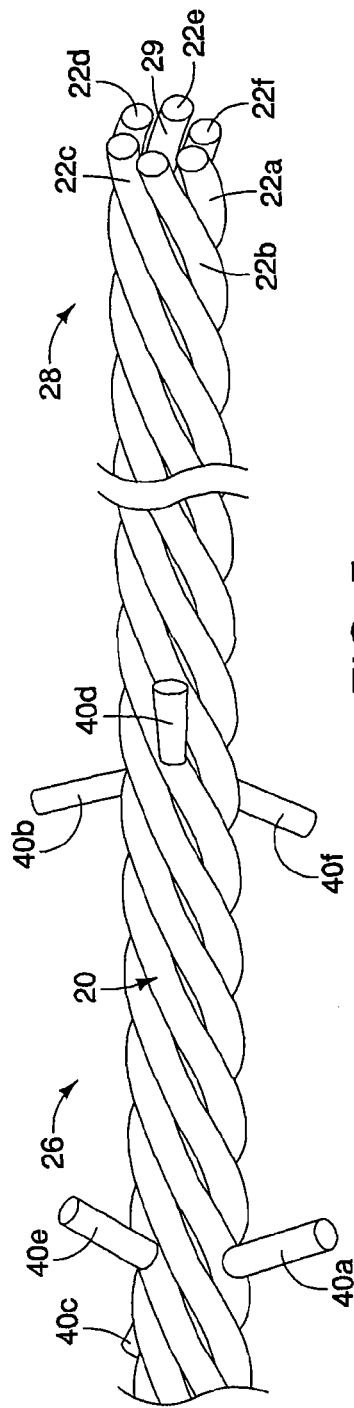
FIG. 5 is a perspective view of the medical device of FIG. 1 having a first set of prongs coupled to a first strand group and a second set of prongs coupled to a second strand group.

As shown in FIG. 5, prongs 40b, 40d and 40f are coupled to the strands 22b, 22d and 22f along their respective proximal regions 26. The prongs 40b, 40d and 40f preferably extend in radially outward directions that are, when used in the 6-wire configuration, offset by about 120 degrees around the circumference of the medical device 20, as depicted in FIG. 5. Similarly, three prongs 40a, 40c and 40e are coupled to the strands 22a, 22c and 22e along their respective proximal regions 26. Notably, the prongs 40a, 40c and 40e are attached to the first group of strands 22a, 22c and 22e at locations that are offset proximally from the point where the prongs 40b, 40d and 40f are attached to the second group of strands 22b, 22d and 22f. The prongs 40a-40f may be attached to their respective strands 22a-22f using any suitable technique, such as a solder or weld, or alternatively may be integrally formed with the strands 22a-22f.

Figure 6:
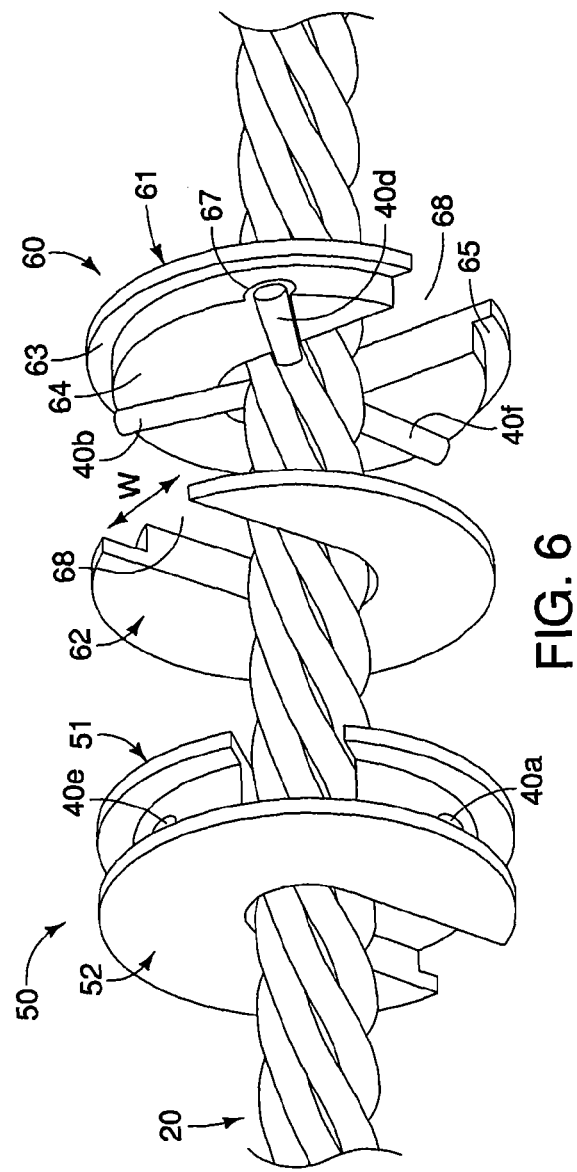
FIG. 6 is an exploded view showing components that may be used to actuate the apparatus of FIG. 5.

Referring now to FIG. 6, an exemplary first coupling assembly 50 may be used to operatively couple to the first group of strands 22a, 22c and 22e, while a second coupling assembly 60 may be used to operatively couple to the second group of strands 22b, 22d and 22f.

The first coupling assembly 50 may comprise complementary first and second segments 51 and 52, while the second coupling assembly 60 may comprise complementary first and second segments 61 and 62. Each of the segments 51, 52, 61 and 62 are substantially identical, and therefore, only features of the first segment 61 of the second coupling assembly 60 will be described in detail.

As can be seen in FIG. 6, the first segment 61 comprises an outer portion 63 and an inner portion 64, each of which are substantially circular in shape. The inner portion 64 comprises a smaller outer diameter relative to the outer portion 63. Accordingly, a recessed ring 65 is formed in the space between the inner and outer portions 64 and 63.

The inner portion 64 comprises three grooved portions 67, which are sized to accommodate at least a portion of the prongs 40b, 40d and 40f. As depicted in FIG. 6, a single grooved portion 67 that is formed in a surface of the inner portion 64 may accommodate approximately one-half of the prong 40d. The remainder of the prong 40d is sized to be received in a complementary groove formed in the inner portion of the complementary second segment 62. Therefore, when the first and second complementary segments 61 and 62 are held in close contact, each of the prongs 40b, 40d and 40f are fully enclosed in a groove formed by two opposing grooved portions 67. Similarly, each of the prongs 40a, 40c and 40e are fully enclosed within grooves of the first coupling assembly 50.

In this manner, when fully assembled, linear and rotational movement of the first coupling assembly 50 yields a corresponding linear and rotational movement of the first group of strands 22a, 22c and 22e. Similarly, linear and rotational movement of the second coupling assembly 60 yields a corresponding linear and rotational movement of the second group of strands 22b, 22d and 22f, independently of the first group of strands.

Figure 7:
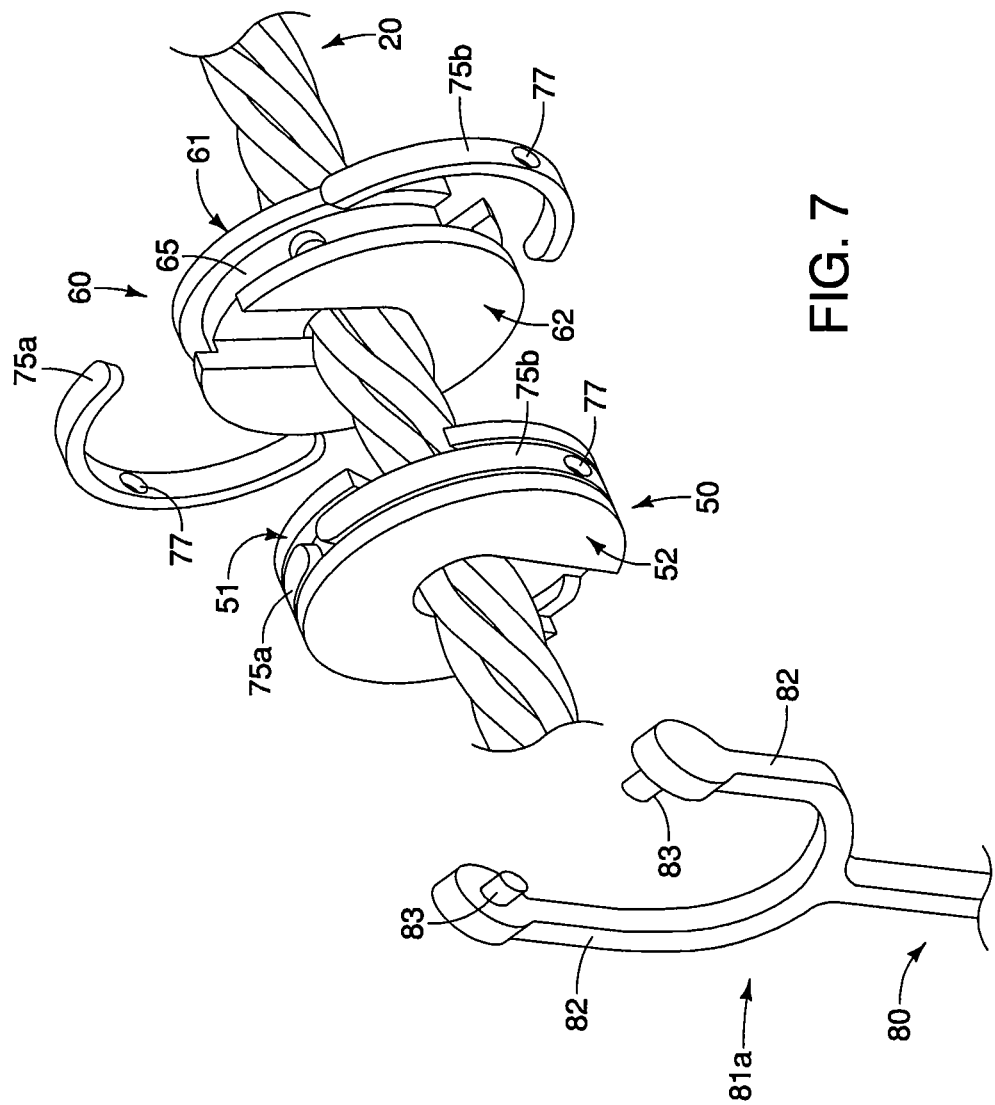
FIG. 7 is a partially exploded view showing further assembly of the apparatus of FIGS. 5-6.

It should be noted that the segments 51, 52, 61 and 62 may each comprise slits 68 formed therein, as shown in FIGS. 6-7, which facilitate positioning of the segments 51, 52, 61 and 62 around the bundle of strands 22a-22f and into engagement with the desired strands. Preferably, the slits 68 comprise a lateral width w, which is slightly larger than an outer diameter of the bundle of strands 22a-22f, as depicted in FIG. 6.

The first and second segments of each coupling assembly may be secured to one another by welding or soldering, or using fasteners, interlocking parts, and the like. In this embodiment, as shown in FIG. 7, two semi-circular clips 75a and 75b may ride within the recessed ring 65 formed between the inner and outer portions 64 and 63. When assembled, the clips 75a and 75b may be secured and slide within the recessed ring 65 of each of the coupling assemblies 50 and 60, for example, using a slip-fit friction engagement.

Figure 8:
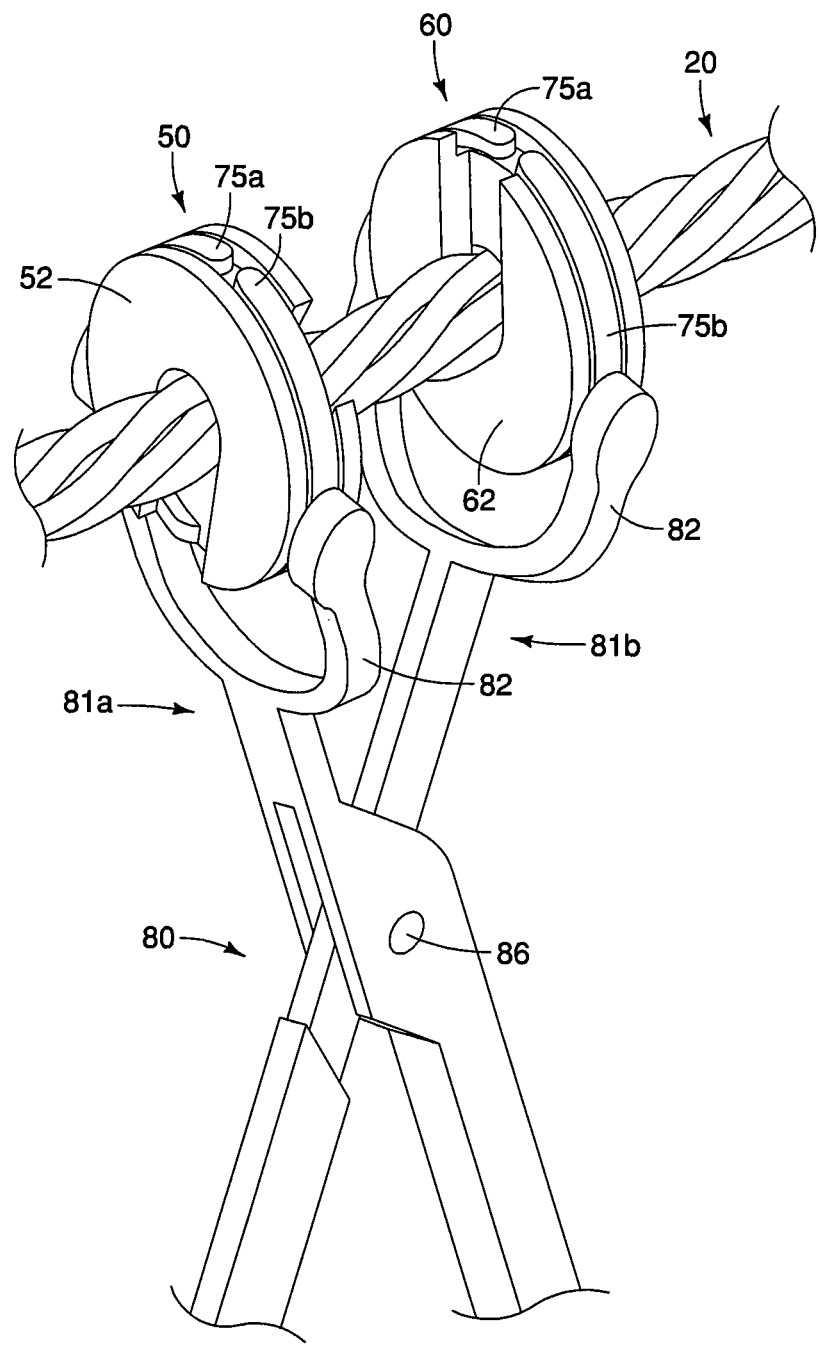
FIG. 8 is a perspective view of a device that may be used to actuate the apparatus of FIGS. 5-6.
Figure 11A:
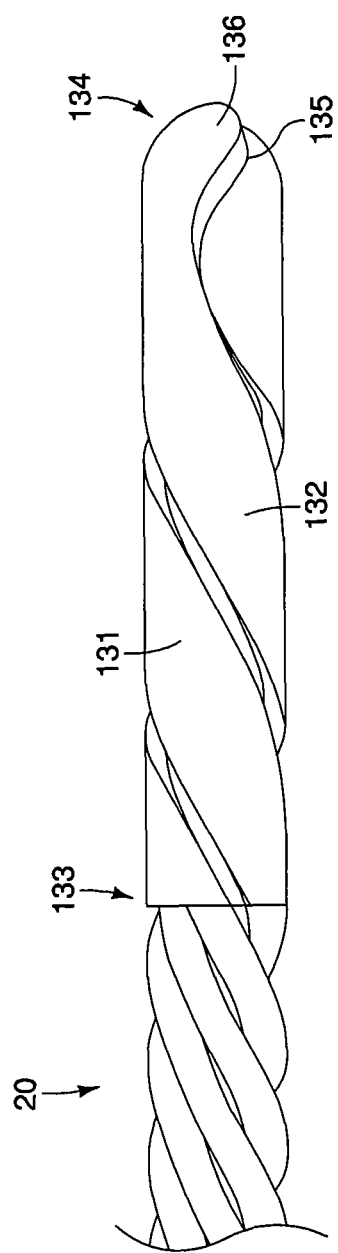
FIGS. 11A-11B are perspective views of an alternative assembly that may be coupled to the medical device of FIG. 1, as shown in retracted and advanced states, respectively.
Figure 11B:
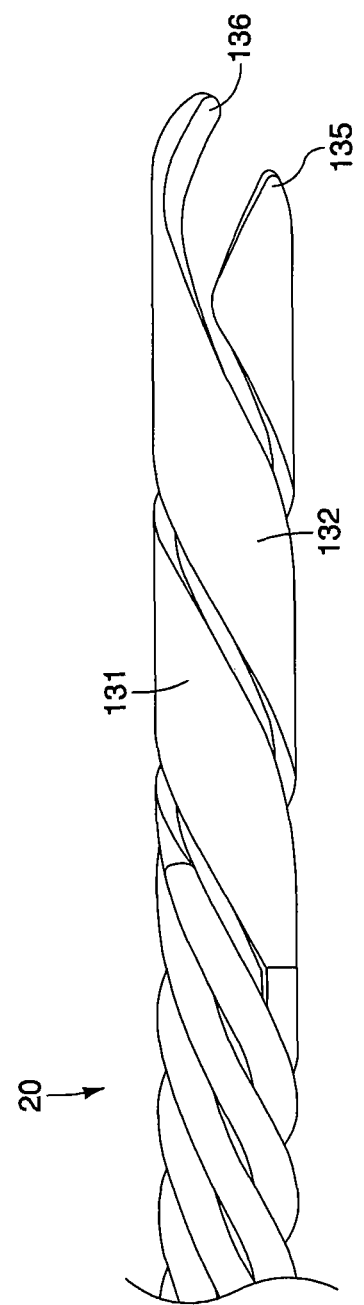
Figure 12A:
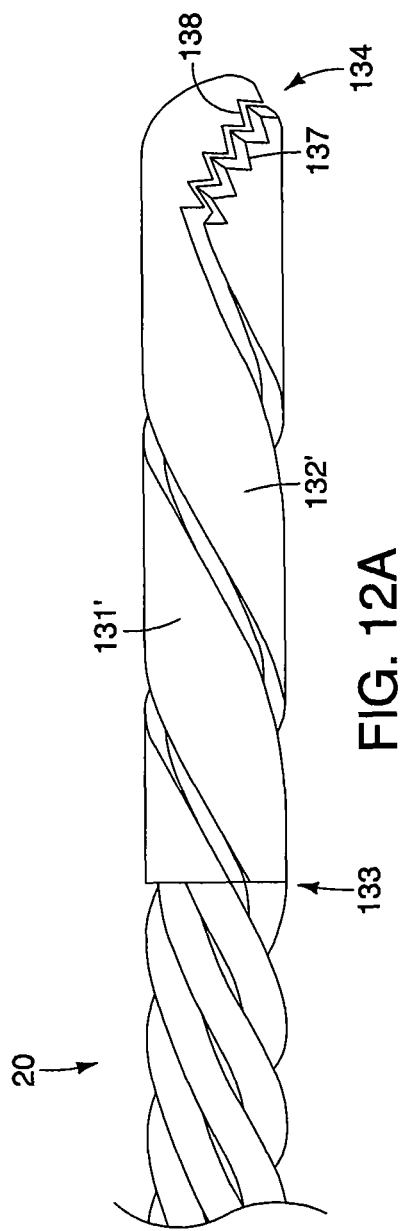
FIGS. 12A-12B are perspective views of an alternative assembly that may be coupled to the medical device of FIG. 1, as shown in retracted and advanced states, respectively.
Figure 12B:
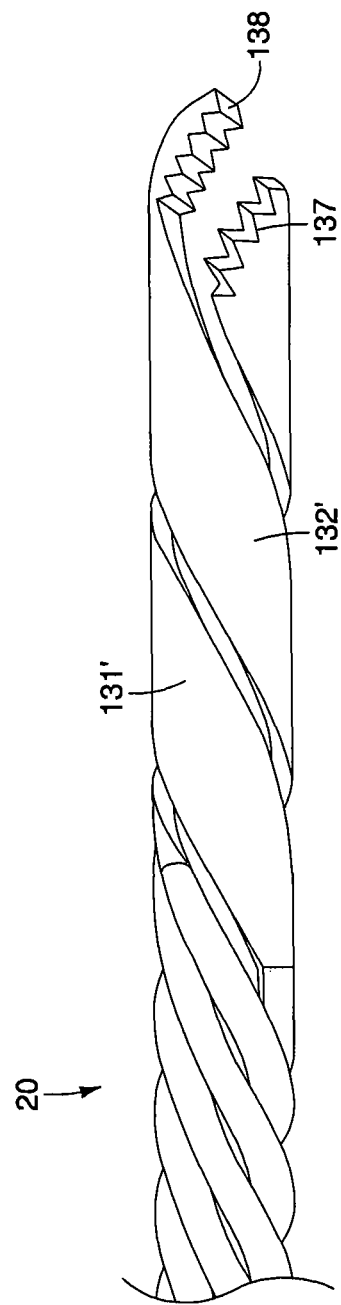

The first and second coupling assemblies 50 and 60 may be actuated manually or using an external actuating device. In the embodiment shown, the clips 75a and 75b comprise one or more bores 77 formed therein, which are adapted to engage an external actuating device. For example, an actuating device 80 may be used. The actuating device 80 may comprise first and second segments 81a and 81b, each having opposing upraised elements 82, as shown in FIGS. 7-8. Knobs 83 may extend inwardly from the upraised elements 82, as shown in FIG. 7, and may engage the bores 77 of the clips 75a and 75b. The actuating device 80 comprises a pivot point 86 to allow the first and second segments 81a and 81b to move relative to one another.

In use, when the actuating device 80 is engaged by a physician, the first and second segments 81a and 81b may move linearly relative to one another, thus urging the first and second coupling assemblies 50 and 60 to move relative to one another. Motion applied to the first segment 81a that is engaged with the first coupling assembly 50 effects corresponding motion upon the first group of strands 22a, 22c and 22e, while motion applied to the second segment 81b coupled to the second coupling assembly 60 effects corresponding motion upon the second group of strands 22b, 22d and 22f. During this movement, the clips 75a and 75b may rotate circumferentially within the recessed rings 65, as the strands move through their respective helical paths. Notably, an interventionalist may move the medical device 20 as a unit either linearly or rotationally, independent of the relative movement between the two groups of strands.

Referring now to FIGS. 9A-9B, an exemplary cutting device 100 that may be coupled to the apparatus of FIG. 1 is shown in retracted and advanced states, respectively. The cutting device 100 comprises a first segment 110 and a second segment 120, wherein the first segment 110 is disposed at least partially within the second segment 120, as shown in FIGS. 9A-9B. The first segment 110 comprises proximal and distal ends 112 and 114, respectively. The proximal end 112 of the first segment 110 may comprise a tubular shape having a lumen 118 therein, while the distal end 114 steps down and comprises a plurality of teeth 115 formed therein, as shown in FIGS. 9A-9B.

Similarly, the second segment 120 comprises proximal and distal ends 122 and 124, respectively. The second segment 120 also comprises a lumen sized to receive the first segment 110 therein, as depicted in FIGS. 9A-9B. The proximal end 122 of the second segment 120 may comprise a tubular shape, while the distal end 124 steps down and comprises a plurality of teeth 125 formed therein.

In accordance with one aspect, the distal regions 28 of each of the first set of strands 22a, 22c and 22e are attached to the proximal end 112 of the first segment 110, as shown in FIGS. 9A-9B. Accordingly, actuation of the first set of strands 22a, 22c and 22e yields a corresponding actuation of the first segment 110. By contrast, the distal regions of each of the second set of strands 22b, 22d and 22f are attached to the proximal end 122 of the second segment 120, such that actuation of the second set of strands 22b, 22d and 22f yields a corresponding actuation of the second segment 120.

In this manner, the first and second segments 110 and 120 of the cutting device 100 may be actuated independently to achieve a desired effect, such as grasping, cutting and the like. While FIGS. 9A-9B depict the advancement of the second cutting segment 120 with respect to the first cutting segment 110, the first cutting segment 110 alternatively may be advanced relative to the second cutting segment 120, or both cutting segments 110 and 120 may be advanced or retracted at the same time. In the state shown in FIG. 9A, the cutting device 100 may be adapted to receive tissue within the stepped down regions of the first and second segments 110 and 120. In FIG. 9B, rotation of the second set of strands 22b, 22d and 22f cause the teeth 125 to rotate circumferentially relative to the teeth 115. Optionally, a stop member may be used to limit distal advancement of the first and second segments 110 and 120 with respect to one another.

Advantageously, the working lumen 29 of the medical device 20 remains unobstructed during actuation of the cutting device 100. Thus, one or more medical components or fluids such as saline may be delivered, or tissue and/or blood may be aspirated, through the working lumen 29 of the strands 22a-22f and through the lumen 118 of the first cutting segment 110. In effect, a cutting or grasping function is achieved by selectively actuating one or more of the strands 22a-22f, without blocking the working lumen 29.

While an exemplary cutting device 100 having first and second segments 110 and 120 is shown coupled to the distal regions of the strands 22a-22f, numerous other devices may be coupled to the distal regions 28 of the strands 22a-22f. The devices need not perform a cutting function, but rather may comprise atraumatic or blunt surfaces adapted to grasp, clamp or otherwise engage tissue. As noted above, both linear and rotational movement may be imparted to whichever tool or device is coupled to one or more of the strands 22a-22f. Moreover, one or more tools or devices may be coupled to one or more of the strands 22a-22f using mechanisms such as bands, clips, adhesives, welds, threads, fasteners, crimps and the like, either removably or permanently.

In an alternative embodiment, an imaging device may be formed integrally with one or more of the strands 22a-22f. For example, as shown in FIG. 2 above, the strand 22a may comprise an integral fiber optic component. Actuation of the proximal region 26 of the strand 22a therefore provides an imaging modality and functionality in both longitudinal and/or angular directions relative to a bodily passageway, without blocking the working lumen 29 and without affecting separate actuation of the other five strands, as desired.

Referring now to FIGS. 10A-10B, an exemplary alternative cutting device 100' is similar to the cutting device 100 of FIGS. 9A-9B, with a main exception that shearing edges 115' and 125' are provided on first and second segments 110' and 120' in lieu of the teeth 115 and 125, respectively. Operation of the alternative cutting device 100' is preferably identical to the operation of the cutting device 100, as described above.

Referring now to FIGS. 11A-11B and 12A-12B, still further alternative devices for use with the medical device 20 described above are shown. In each of these embodiments, first and second thin-walled helical ribbons 131 and 132 are provided. The distal regions 28 of each of the first set of strands 22a, 22c and 22e are attached to the proximal end 133 of the first helical ribbon 131, as generally explained in FIGS. 9A-9B above. Accordingly, actuation of the first set of strands 22a, 22c and 22e yields a corresponding actuation of the first helical ribbon 131. By contrast, the distal regions 28 of each of the second set of strands 22b, 22d and 22f are attached to the proximal end 133 of the second helical ribbon 132, such that actuation of the second set of strands 22b, 22d and 22f yields a corresponding actuation of the second helical ribbon 132. Notably, the distal ends 134 of the first and second helical ribbons 131 and 132 of FIGS. 11A-11B comprise edges 135 and 136 that may be used for grasping or shearing, while the distal ends of the first and second helical ribbons 131' and 132' of FIGS. 12A-12B comprise teeth 137 and 138 that may be used for cutting. While grasping, shearing and cutting teeth are shown, numerous other configurations may be provided.

Figure 13:
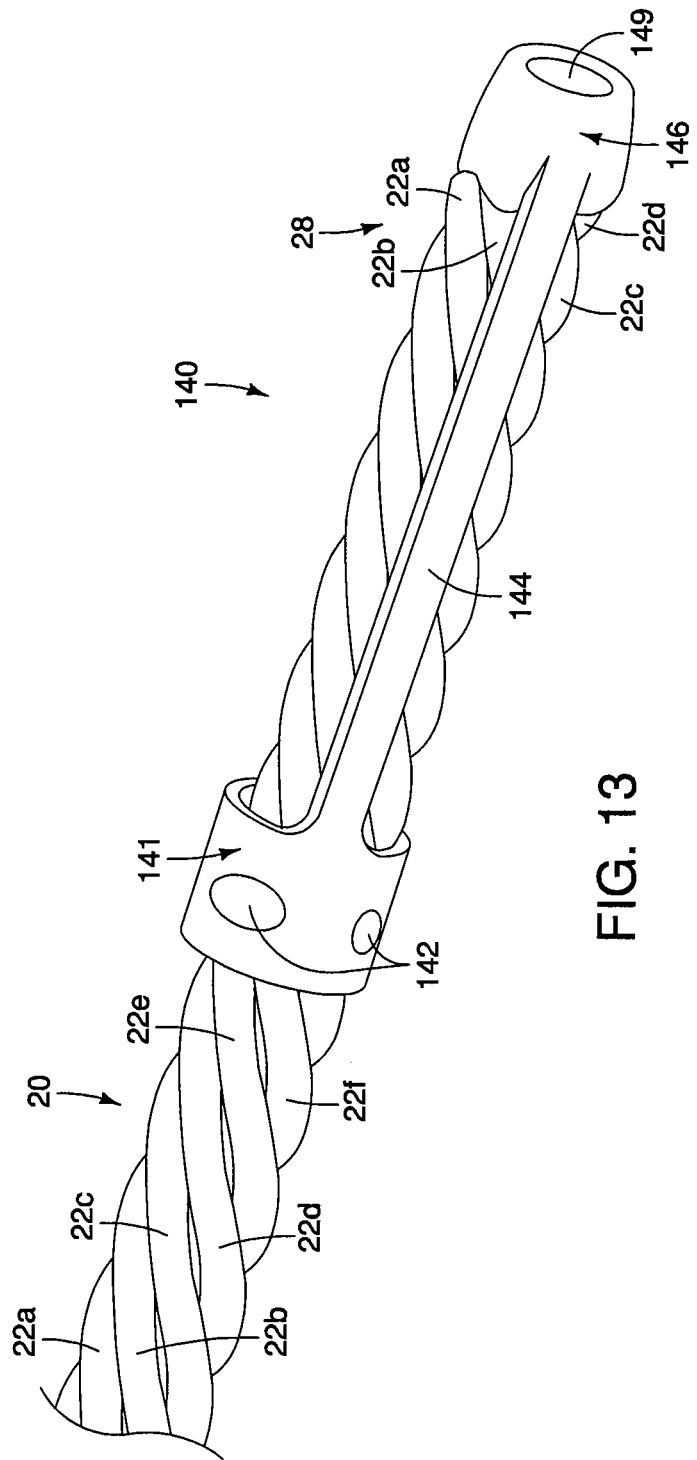
FIG. 13 is an upper perspective view of a steering member that may be coupled to the medical device of FIG. 1.

Referring now to FIG. 13, in an alternative embodiment, a steerable member 140, which may be deflectable, may be used to facilitate insertion and delivery of the medical device 20 to a target site. The steerable member 140 may comprise a proximal region having a cuff 141, a distal region having an atraumatic tip 146, and a flat wire 144 extending therebetween. The cuff 141 may comprise an inner diameter that is slightly larger than an outer diameter of the medical device 20, thereby allowing the cuff 141 to be positioned over the strands 22a-22f. The cuff 141 may comprise attachment points 142 that securely attach the steerable member 140 to the strands 22a, 22c and 22e, causing these strands to be fixed together. In this embodiment, the attachment points 142 comprise bores formed in the cuff 141, whereby an adhesive, solder or weld may be placed within the bores to securely attach the cuff 141 to the strands 22a, 22c and 22e. Further, the distal regions 28 of the strands 22b, 22d and 22f may be securely coupled to the atraumatic tip 146, as depicted in FIG. 13.

In use, the medical device 20 may be advanced over a wire guide, which may extend through the working lumen 29 of the device 20 and also through the lumen 149 of the atraumatic tip 146. The strands 22a, 22c and 22e may be retracted relative to the strands 22b, 22d and 22f, causing the tip to be deflected to the side possessing the flat wire feature 144. The atraumatic tip 146 protects a vessel or duct from being traumatized by the distal ends of the strands 22a-22f. Subsequently, the wire guide then may be removed so that other components may be advanced through the lumens 29 and 149. If the device 20 is used in the gastrointestinal tract, an endoscope having fiber optic components may be used to deliver the device 20 through an auxiliary lumen of the endoscope.

It should be noted that while six total strands 22a-22f are depicted herein, greater or fewer strands may be employed. Solely by way of example, in the embodiments of FIGS. 9-10, four total strands may be employed, wherein two sets of opposing strands are coupled together.

While various embodiments of the invention have been described, it will be apparent to those of ordinary skill in the art that many more embodiments and implementations are possible within the scope of the invention. Accordingly, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. Apparatus suitable for use in a medical procedure, the apparatus comprising:
   an elongate medical device for introduction into a patient, the elongate medical device comprising a plurality of strands, each having proximal and distal regions, wherein the plurality of strands are twisted in a generally helical manner to form a tubular shape having a longitudinal axis, wherein in a cross-section transverse to the longitudinal axis each of the strands forms a portion of an outer circumference of the tubular shape;
   wherein a first strand of the plurality of strands is moveable with respect to at least a second strand of the plurality of strands,
   wherein each of the strands are oriented in a uniform helical direction;
   a first group of strands comprising at least two of the plurality of strands, wherein the first group of strands is coupled together to move in unison with each other; and
   a second group of strands comprising at least two of the plurality of strands, wherein the second group of strands is coupled together to move in unison with each other,
   wherein the first group of strands is movable with respect to the second group of strands.

2. The apparatus of claim 1 wherein the first group of strands is disposed in a circumferentially alternating arrangement with the second group of strands such that no two strands of the first group of strands are adjacent to one another and no two strands of the second group of strands are adjacent to one another.

3. The apparatus of claim 1 further comprising:
   a first coupling assembly operatively coupling each strand of the first group of strands together; and
   a second coupling assembly operatively coupling each strand of the second group of strands together,
   wherein the first and second coupling assemblies may be independently engaged to selectively actuate the first and second group of strands, respectively.

4. The apparatus of claim 1 further comprising a cutting device, wherein a first segment of the cutting device is coupled to the first group of strands and a second segment of the cutting device is coupled to the second group of strands.

5. The apparatus of claim 1 wherein at least one of the strands comprises an integral fiber optic component.

6. The apparatus of claim 1 wherein each strand of the first group of strands comprises a larger cross-sectional diameter than each strand of the second group of strands.

7. The apparatus of claim 1 further comprising a lumen formed within the plurality of strands and along the longitudinal axis, wherein the lumen is sized for the delivery of at least one medical component.

8. Apparatus suitable for use in a medical procedure, the apparatus comprising:
   an elongate medical device for introduction into a patient, the elongate medical device comprising a plurality of strands each having proximal and distal regions, wherein the plurality of strands are twisted in a generally helical manner to form a tubular shape having a longitudinal axis, wherein in a cross-section transverse to the longitudinal axis each of the strands forms a portion of an outer circumference of the tubular shape,
   wherein a first strand of the plurality of strands is moveable with respect to at least a second strand of the plurality of strands,
   wherein at least a third strand is coupled to the first strand to form a first group of strands that move in unison with each other,
   wherein at least two additional strands are coupled together to form a second group of strands that move in unison with each other,
   wherein the first group of strands is movable with respect to the second group of strands, and
   wherein the first group of strands is disposed in a circumferentially alternating arrangement with the second group of strands such that no two strands of the first group of strands are adjacent to one another and no two strands of the second group of strands are adjacent to one another.

9. The apparatus of claim 8 further comprising a lumen formed within the plurality of strands and along the longitudinal axis, wherein the lumen is sized for the delivery of at least one medical component, and wherein the lumen remains unobstructed during movement of the first strand.

10. The apparatus of claim 8 further comprising a cutting device, wherein a first segment of the cutting device is coupled to the first group of strands and a second segment of the cutting device is coupled to the second group of strands.

11. The apparatus of claim 8 further comprising:
   a first coupling assembly operatively coupled to at least the first strand; and
   a second coupling assembly operatively coupled to at least the second strand,
   wherein the first and second coupling assemblies may be independently engaged to selectively actuate the first and second strands, respectively.

12. The apparatus of claim 8 wherein the first strand comprises an integral fiber optic component.

* * * * *